US007932720B2

(12) United States Patent
James et al.

(10) Patent No.: US 7,932,720 B2
(45) Date of Patent: Apr. 26, 2011

(54) MAGNETIC FIELD GRADIENT STRUCTURE CHARACTERISTIC ASSESSMENT USING ONE DIMENSIONAL (1D) SPATIAL-FREQUENCY DISTRIBUTION ANALYSIS

(75) Inventors: Timothy W. James, Swansea (GB); David Chase, Santa Barbara, CA (US)

(73) Assignee: Acuitas Medical Limited, Swansea, Wales (GB)

( * ) Notice: Subject to any disclaimer, the term of this patent is extended or adjusted under 35 U.S.C. 154(b) by 936 days.

(21) Appl. No.: 11/605,804

(22) Filed: Nov. 27, 2006

(65) Prior Publication Data

US 2007/0167717 A1 Jul. 19, 2007

Related U.S. Application Data

(60) Provisional application No. 60/597,349, filed on Nov. 27, 2005, provisional application No. 60/743,779, filed on Mar. 25, 2006.

(51) Int. Cl.
*G01V 3/00* (2006.01)
(52) U.S. Cl. ........ 324/309; 324/307; 324/303; 324/312; 600/410; 600/411
(58) Field of Classification Search .......... 324/300–322; 600/407–435; 382/128–131; 342/179
See application file for complete search history.

(56) References Cited

U.S. PATENT DOCUMENTS

| 4,254,778 A | 3/1981 | Clow et al. |
| 4,296,378 A | 10/1981 | King |
| 4,498,048 A | 2/1985 | Lee et al. |
| 4,621,236 A | 11/1986 | Halbach |
| 4,691,162 A * | 9/1987 | Van Uijen ..................... 324/309 |
| 4,707,663 A | 11/1987 | Minkoff et al. |
| 4,868,501 A | 9/1989 | Conolly |
| 4,980,641 A | 12/1990 | Breneman et al. |
| 5,095,271 A | 3/1992 | Ohkawa |
| 5,099,208 A | 3/1992 | Fitzpatrick et al. |
| 5,150,053 A * | 9/1992 | Pauly et al. ................... 324/309 |

(Continued)

FOREIGN PATENT DOCUMENTS

EP 1 308 743 A1 5/2003

(Continued)

OTHER PUBLICATIONS

"International Search Report and Written Opinion of the International Searching Authority Dated Jun. 16, 2006" International Application No. PCT/US2006/000624, (Jun. 16, 2006).

(Continued)

*Primary Examiner* — Melissa J Koval
*Assistant Examiner* — Tiffany A Fetzner
(74) *Attorney, Agent, or Firm* — Blakely Sokoloff Taylor & Zafman LLP

(57) ABSTRACT

The disclosed innovation is a method for acquiring spatial frequency spectra from specific locations in a 3D sample using modifications of the current MRI techniques for localized NMR spectroscopy. The innovation in its simplest abstraction is to add the use of a read out gradient to the current NMR spectroscopy pulse sequences and record the resultant echo. These techniques generate spectra from a selected region or generate an image of the results over a region of the sample. These methods can be applied to analyzing the structure of trabecular bone as well as for analyzing or diagnosing disease in cases where there is a difference in the spatial frequency power spectrum due to physiologic or disease processes. Various embodiments are disclosed.

19 Claims, 11 Drawing Sheets

U.S. PATENT DOCUMENTS

| | | | |
|---|---|---|---|
| 5,184,074 | A | 2/1993 | Kaufman et al. |
| 5,207,224 | A | 5/1993 | Dickinson et al. |
| 5,304,930 | A | 4/1994 | Crowley et al. |
| 5,384,573 | A * | 1/1995 | Turpin .......................... 342/179 |
| 5,493,225 | A | 2/1996 | Crowley et al. |
| 5,736,958 | A * | 4/1998 | Turpin .......................... 342/179 |
| 5,821,751 | A * | 10/1998 | Wendt et al. .................. 324/307 |
| 5,879,299 | A | 3/1999 | Posse et al. |
| 5,999,838 | A | 12/1999 | Crowley et al. |
| 6,081,117 | A | 6/2000 | Crowley et al. |
| 6,185,444 | B1 | 2/2001 | Ackerman et al. |
| 6,285,901 | B1 | 9/2001 | Taicher et al. |
| 6,777,934 | B2 * | 8/2004 | Takahashi et al. ............ 324/309 |
| 7,723,987 | B2 * | 5/2010 | Bito et al. ...................... 324/309 |
| 2002/0107438 | A1 | 8/2002 | Liu et al. |
| 2002/0191823 | A1 | 12/2002 | Wehrli et al. |
| 2003/0052676 | A1 * | 3/2003 | Takahashi et al. ............ 324/307 |
| 2003/0162224 | A1 | 8/2003 | Chait et al. |
| 2004/0024305 | A1 | 2/2004 | Elgort et al. |
| 2005/0240096 | A1 | 10/2005 | Ackerman et al. |
| 2007/0167717 | A1 * | 7/2007 | James et al. .................. 600/407 |
| 2008/0272775 | A1 * | 11/2008 | Feng .............................. 324/307 |
| 2009/0085563 | A1 * | 4/2009 | Bito et al. ...................... 324/307 |
| 2009/0136104 | A1 * | 5/2009 | Hajian et al. .................. 382/128 |
| 2010/0141256 | A1 * | 6/2010 | Feng .............................. 324/309 |

FOREIGN PATENT DOCUMENTS

| | | |
|---|---|---|
| GB | 2 056 081 A | 3/1981 |
| GB | 2 345 757 A | 7/2000 |
| JP | 11-239568 | 9/1999 |
| RU | 2122203 | 11/1998 |
| WO | WO - 99/45842 | 9/1999 |
| WO | WO - 2004/095049 A1 | 11/2004 |

OTHER PUBLICATIONS

"International Search Report and Written Opinion of the International Searching Authority Dated Jul. 24, 2007", International Application No. PCT/US2006/045563, (Jul. 24, 2007).

Banerjee, S., et al., "High Resolution MR imaging of trabecular bone using steady state free precession (SSFP) at 1.5T and 3T" *2004 Proceedings of the International Society of Magnetic Resonance in Medicine*, (2004), p. 427.

Benito, Maria, et al., "Deterioration of Trabecular Architecture in Hypogonadal Men", *The Journal of Endocrinology & Metabolism*, vol. 88, No. 4, (Apr. 2003), pp. 1497-1502.

Faulkner, Kenneth G., et al., "Future methods in the assessment of bone mass and structure", *Best Practice & Research Clinical Rheumatology*, vol. 15, No. 3, (2001), pp. 359-383.

Gomberg, Bryon R., et al., "Integrated Processing Systems of in Vivo MR Images of Trabecular Bone Networks", *2001 ISMRM 9th Meeting and Exhibition, Glasgow, Scotland*(2001).

Gomberg, B.R., et al., "Reproducibility and error sources of u-MRI-based trabecular bone structural parameters of the distal radius and tibia", *Bone*, vol. 35, (2004), pp. 266-276.

Gomberg, Bryon R., et al., "Topological Analysis of Trabecular Bone MR Images", *IEEE Transactions on Medical Imaging*, vol. 19, No. 3, (2000), pp. 166-174.

Gomberg, Bryon R., et al., "Topology-based orientation analysis of trabecular bone networks", *Medical Physics*, vol. 30, No. 2, (Feb. 2003), pp. 1-11.

Hwang, Scott N., et al., "Estimating Voxel Volume Fractions of Trabecular Bone on the Basis of Magnetic Resonance Imgaes Acquires in Vivo", *International Journal of Imaging Systems & Technology*, vol. 10, (1999), pp. 186-198.

Hwang, Scott N., et al., "Probability-based structural parameters from three-dimensional nuclear dimensional nuclear magnetic resonance images as predictors of trabecular bone strength", *Medical Physics*, vol. 24, No. 8, (Aug. 1997), pp. 1255-1261.

Hwang, Scott N., et al., "Subvoxel Processing: A Method for Reducing Partial Volume Blurring with Application to In Vivo MR Images of Trabecular Bone", *Magnetic Rseonance in Medicine*, vol. 47, (2002), pp. 948-957.

Krug, R., et al., "In vivo measurement of trabecular bone microarchitecture in the proxiamal femur with MRI at 1.5 T and 3 T", *2004 Proceedings of the International Society of Magnetic Resonance in Medicine*, (2004), p. 801.

Ma, Jingfei, et al., "Fast 3D Large-Angle Spin-Echo Imaging (3D FLASE", *Magnetic Resonance in Medicine*, vol. 3, (1996), pp. 903-910.

Majumdar, Sharmila, et al., "Fractal analysis of radiographs: Assessment of trabecular bone structure and prediction of elastic modulus and strength", *Medical Physics*, vol. 26, No. 7, (Jul. 1999), pp. 1330-1340.

Majumdar, S., et al., "High resolution magnetic resonance imaging of trabecular structure", *European Radiology*, vol. 7, Suppl. 2, (1997), pp. S51-S55.

Saha, P.K., et al., "3D Digital Topology under Binary Transformation with Applications", *Computer Vision and Image Understanding*, vol. 63, No. 3, Article No. 0032, (May 1996), pp. 418-429.

Saha, P.K., et al., "A New Shape Preserving Parallel Thinning Algorithm for 3D Digital Images", *Pattern Recognition*, vol. 30, No. 12, (1997), pp. 1939-1955.

Saha, Punam K., et al., "Fuzzy Distance Transform: Theory, Algorithms, and Applications", *Computer Vision and Image Understanding*, vol. 86, (2002), pp. 171-190.

Saha, Punam K., et al., "Three-Dimensional Digital Topological Characterization of Cancellous Bone Architecture", *International Journal of Imaging Systems & Technology*, vol. 11, (2000), pp. 81-90.

Song, Hee K., et al., "In Vivo Micro-Imaging Using Alternating Navigator Echoes With Applications to Cancellous Bone Stucture Analysis", *Magnetic Resonance in Medicine*, vol. 41, (1999), pp. 947-953.

Wehrli, Felix W., et al., "Digital Topological Analysis of In Vivo Magnetic Resonance Microimages of Trabecular Bone Reveals Structural Implications of Osteoporosis", *Journal of Bone and Mineral Research*, vol. 16, No. 8, (2001), pp. 1520-1531.

Wehrli, F.W., et al., "Longitudinal Changes in Trabecular Bone Architecture Detected by Micro-MRI Based Virtual Bone Biopsy", *25th Annual Meeting of the American Society for Bone and Mineral Research*, (2003).

Wehrli, Felix W., et al., "Quantitative High-Resolution Magnetic Resonance Imaging Reveals Structural Implications of Renal Osteodystrophy on Trabecular and Cortical Bone", *Journal of Magnetic Resonance Imaging*, vol. 20, (2004), pp. 83-89.

Wehrli, Felix W., et al., "Role of Magnetic Resonance for Assessing Structure and Function of Trabecular Bone", *Topics in Magnetic Resonance Imaging*, vol. 13, No. 5, (2002), pp. 335-355.

Wen, C.Y., et al., "Self-similar texture characterization using a Fourier-domain maximum likelihood estimation method", *Pattern Recognition Letters*, vol. 19, No. 8, (Jun. 1998), pp. 735-739.

R. Pohmann et al., "Theoretical Evaluation and Comparison of Fast Chemical Shift Imaging Methods", Journal of Magnetic Resonance, 1997, vol. 129, pp. 145-160.

Sumi Bao et al., "Spin-Echo Planar Spectroscopic Imaging for Fast Lipid Characterization in Bone Marrow", Magnetic Resonance Imaging, 1999, vol. 17, No. 8, pp. 1203-1210.

J. S. Gregory et al., "Analysis of Trabecular Bone Structure Using Fourier Transforms and Neural Networks", IEEE Transactions on Information Technology in Biomedicine, Dec. 1999, vol. 3, No. 4, pp. 289-294.

Dick J. Drost et al., "Proton magnetic resonance spectroscopy in the brain: Report of AAPM MR Task Group #9", Medical Physics, Sep. 2002, vol. 29, No. 9, pp. 2177-2197.

Johannessen, Espen H., et al., "Probing structural periodicity (annual ring size) in Scots pine by NMR profiling", *Wood and Science Technology*, vol. 40, (Jan. 27, 2006), pp. 537-547.

"Office Action of The Federal Institute for Industrial Property of The Federal Service for Intellectual Property, Patents and Trademarks (Russian Federation) Dated Oct. 13, 2010", Application No. 2008126110.

"Office Action of the State Intellectual Property Office of the People's Republic of China Dated Oct. 15, 2010", Application No. 200680051737.X.

"Decision on Grant of The Federal Institute for Industrial Property of The Federal Service for Intellectual Property, Patents and Trademarks (Russian Federation) Dated Jan. 20, 2011" Application No. 2008126110.

\* cited by examiner

Iso-B₀ Non-linear Slices

— 1 mm

MAGNETIC FIELD GRADIENT STRUCTURE CHARACTERISTIC ASSESSMENT USING ONE DIMENSIONAL (1D) SPATIAL-FREQUENCY DISTRIBUTION ANALYSIS

CROSS-REFERENCE TO RELATED APPLICATION

This application claims the benefit of U.S. Provisional Patent Application No. 60/597,349 filed Nov. 27, 2005 and also claims the benefit of U.S. Provisional Patent Application No. 60/743,779 filed Mar. 25, 2006.

BACKGROUND OF THE INVENTION

1. Field of the Invention

The present invention relates to the field of diagnostic assessment of complex biological and physical structures, including bone strength in patients at risk of or suffering from osteoporosis and other conditions that degrade the trabecular structure of cancellous bone. Additional structures include evaluating vasculature in tumors, and hydrocarbon pore distributions in strata.

2. Prior Art

The trabecular architecture is both highly sensitive to metabolic changes in bone (relative to the more dense outer shell of cortical bone) and a major contributor to the overall strength of a bone. Hence it is an appropriate surrogate marker for tracking disease and treatment.

The Impact of Bone Disease Diseases of the skeletal system, including osteoporosis and other less common conditions, are a major threat to the health of the elderly, particularly women. The significance of bone disease is evident from the 2004 Surgeon General's report, "Bone Health and Osteoporosis," and from the declaration of 2002-2011 as the Decade of the Bone and Joint. More than 10 million Americans over age 50 suffer from osteoporosis (the weakening of the skeletal system as a result of loss of bone mass), and an additional 34 million are at risk. More than 1.5 million fractures occur each year as a result of osteoporosis, with direct costs of care of approximately $15 billion, and billions more in costs associated with loss of productivity and the three-fold increase in risk of mortality associated with fractures. The continuing aging of the population will cause the number of fractures and the associated economic and societal impact to more than double by 2020, with at least 50% of the population over the age of 50 suffering from, or at risk of, osteoporosis.

Diagnosis and Treatment of Osteoporosis The cycle of bone production goes through a number of stages, typically peaking in the early twenties and declining gradually thereafter. In middle age, and particularly in post-menopausal women, the net production of bone can become negative, and the trabecular bone, the structure of rods and plates that supports the outer shell of cortical bone, becomes thinner and weaker. The loss of bone strength that results from the thinned and more porous bone structure in osteoporotic bone increases the risk of fracture in vulnerable regions such as the hip and spine. Although the hip and spine exhibit most of these fractures, they are more difficult to image than the calcaneous (heel bone) and distal radius. Since osteoporosis is a systemic metabolic disease, and the weight-bearing bones are good indicators of the disease state, images of either of these bones are indicative of the progression of the disease in the patient's skeletal system as a whole. The calcaneous is a particularly good bone for assessing trabecular architecture, as it is a weight-bearing bone and relatively accessible for imaging using an MRI (magnetic resonance imager or magnetic resonance imaging).

Osteoporosis is not an inevitable consequence of aging. Proper lifestyle choices, including smoking cessation, moderate exercise, and adequate doses of calcium and vitamin D, can reduce bone loss and fracture risk. Several drugs are also available for the treatment of osteoporosis. Bisphosphonates, including Fosamax™ and Actonel™, are oral agents that reduce the resorption of bone. Teriparatide, marketed under the name Forteo™, is an anabolic hormone extract that stimulates bone growth but must be administered by daily injection. Other forms of hormone therapy also stimulate development of bone but carry significant risk of side effects as shown in recent clinical trials.

Proper therapy requires timely and accurate diagnosis. The current standard in diagnosis of osteoporosis is measurement of bone mineral density (BMD) by dual energy x-ray absorptiometry (DEXA). Recent studies in the USA have indicated that DEXA is underutilized, with less than 25% of the at-risk population receiving BMD testing, due partially to the cost of DEXA but primarily to lack of awareness. Of much greater concern is the fact that physicians have begun to question the clinical relevance of DEXA, based on emerging evidence that DEXA measurements do not properly predict fracture risk and are particularly inadequate in assessing the effectiveness of therapy.

As a result of these concerns, a number of other imaging modalities, including quantitative computed tomography, ultrasound, and magnetic resonance imaging are being explored as alternatives to DEXA. The resistance of bone to fracture depends, as is the case for most materials, not just on density but also on the structure of the bone, including the relative fractions of, and the thickness and orientation of, trabecular rods and plates. MRI, which is inherently a three-dimensional technique, is well suited to the determination of the structural details that determine fracture resistance.

The MRI techniques currently being investigated for diagnosis of osteoporosis require the acquisition of extremely high-resolution images, as well as requiring a number of image processing operations. Images of living bone can be acquired in a high-field MRI system using specialized coils, and lengthy exam times. Careful patient positioning and stabilization are also required. These high-field systems cost around $2 million and need to be housed in carefully controlled environments overseen by radiology specialists. The invention reported here enables devices that can be housed in a typical doctor's office and which cost less than $200,000.

Magnetic Resonance (MR) in some ways is particularly well suited to measuring living bone, as hard-bone (i.e., the calcified structure of the trabeculae and cortical bone) gives very low signal, while marrow (which fills the spaces between the trabecular lattice) gives high signals, hence providing good contrast and good signal to noise. But the high cost of high-field systems, and the need for long acquisition times in order to resolve fine structures combined with the requirement that the patient (imaged body part) not move during acquisition, yield a level of impracticality in the implementation of standard MRI for this purpose.

MRI is based on an extension of the mathematics of Fourier expansion which states that a one-dimensional repetitive waveform (e.g., a signal amplitude as a function of time or an intensity as a function of linear position) can be represented as the sum of a series of decreasing period (increasing frequency) sinusoidal waveforms with appropriate coefficients (k-values).

In MRI, the item (body part) to be imaged is a three-dimensional object. The basic concept of k-values in one dimension can be extended to two or three dimensions. Now, rather than a series of k-values, there is a two or three-dimensional matrix of k-values, each k-value representing a particular spatial frequency and direction in the sample.

In Fourier analysis, converting from the k-values to the desired waveform (amplitude vs. time for a time varying signal or image intensity vs. position for the MRI case) is accomplished by using a Fourier transform. The Fourier transform in simple terms is a well-known means to convert between the frequency domain and time domain (for time varying signals). For images, as in the MRI case, the Fourier transform is used to convert between the spatial-frequency domain (the series of sinusoidal waveforms and their coefficients, referred to as k-space) and the spatial arrangement of signal intensities for each of the imaged volumes (voxels). Similar to the case of time-varying signals, where the k-values are coefficients for the sinusoidal waveforms with given periods, the k-values in the MRI case are the coefficients for the sinusoidal waveforms with given wave lengths (where the wavelengths are inversely related to spatial frequencies, i.e., a long wavelength is a low spatial frequency).

MRI technology today uses a number of methods to acquire images. Virtually all rely on gathering the k-space coefficients and later Fourier transforming them into an image (or set of images as in a 3D acquisition). In the simplest abstraction, this is accomplished by placing the part to be imaged in a strong magnetic field and exciting the hydrogen nuclei in the sample by transmitting at the sample a pulsed radio-frequency electromagnetic signal tuned to the resonant frequency of the hydrogen nuclei. This pulse starts the nuclei resonating at their resonant frequency. Then, to obtain information about where in the sample the signal originates from, the spins of the excited hydrogen atoms are encoded with a combination of phase and frequency encodes corresponding to the desired k-space data being acquired on that excitation. (Here phase and frequency refer to the resonant frequency and phase of the hydrogen nuclei). This is accomplished by modulating the magnetic field spatially and temporally, so as to correspondingly spatially alter the resonant frequency of the nuclei and modulate their phase. A signal is received back then from the excited hydrogen nuclei of the sample, and the k-values are extracted from the signal. This process of excitation, encoding, and signal acquisition is repeated until an entire matrix of k-space values (properly selected to constitute a Fourier series) is acquired with sufficiently high spatial frequency to resolve the desired features in the sample. Finally, the matrix of k-values is Fourier transformed to produce an image or images. There are many variations and extensions of this theme in use in current technology MRI systems. One approach utilizes frequency encoding to localize signals to thin slices and phase encoding to generate the k-values for each of these 2D slices.

DETAILED DESCRIPTION OF THE PREFERRED EMBODIMENTS

As noted above, this application claims priority on two provisional applications. The first provisional describes a technique and apparatus for characterizing the size distributions of a dispersed NMR signal producing phase intermingled with one or more additional phases with significantly different signal properties. Examples are marrow in cancellous bone and petroleum dispersed in strata.

The approach involves the following components: First, provide a magnetic field ($B_0$) covering the region of interest (ROI) in a sample desired to be characterized. Second, provide a gradient in $B_0$ over the ROI. Third, provide transmit (excitation) and receive antennas/systems that have a net high sensitivity to signals excited in and emanating from the ROI.

Using this apparatus, perform an NMR experiment by transmitting a defined bandwidth pulse to excite the NMR signal in the desired range of $B_0$, followed by one or more refocusing transmit pulses and sampling of the received echo. Alternatively this can be done with a gradient echo method. The samples of this echo provide a line in k-space representative of the Fourier transform of the NMR signal intensity emanating from the ROI along the direction of the gradient in $B_0$.

The NMR experiment descried above can be preformed in one or more directions or locations (ROI) in the sample to assess the spatial frequency content and its homogeneity and anisotropy in the sample.

The following paragraphs describe and derive the relationship between the signal and spatial frequency distribution in the ROI in a single gradient configuration.

Figure 1:
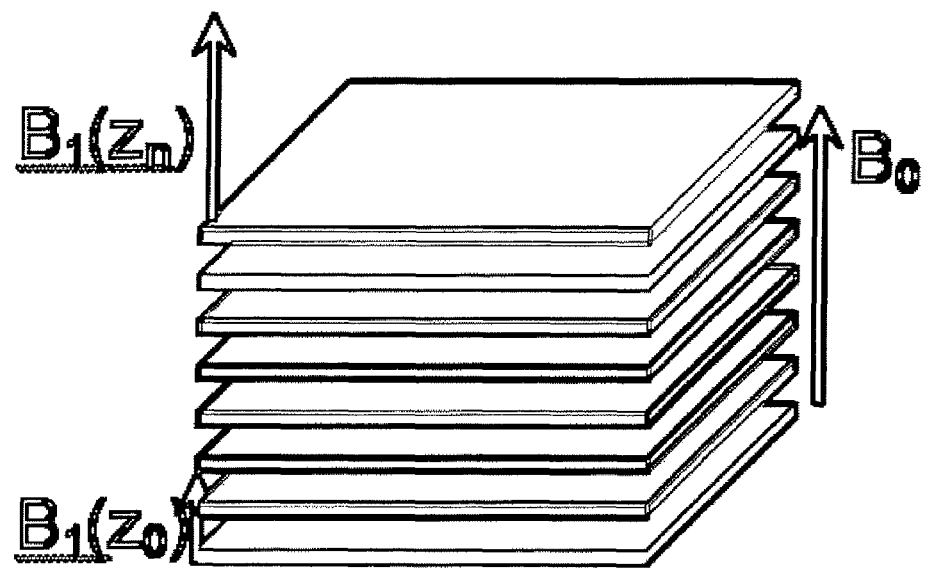
FIG. 1 illustrates linear surface Iso-$B_0$ slices.
Figure 2:
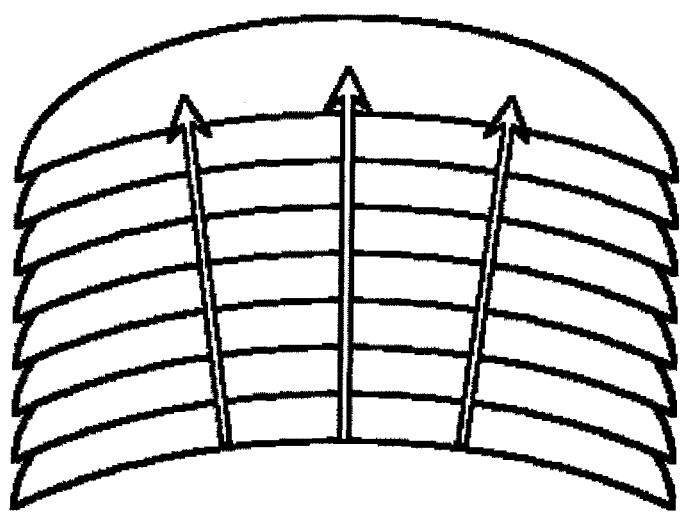
FIG. 2 illustrates nonlinear surface Iso$B_0$ slices.

In this approach, assume that there is one dimension wherein one can achieve some special discernment through the use of a frequency gradient. The remaining two dimensions form a surface which, added to the 'thickness' associated with the frequency gradient, creates a slice in space which does not necessarily have to be linear in Euclidian space. This is illustrated in FIG. 1 (Iso-$B_0$ Linear Slices [surfaces] with added linear gradient) and in FIG. 2 (Iso-$B_0$ Nonlinear Slices [surfaces]).

The slice's geometry is influenced not only by the main magnetic field ($B_0$) uniformity (or lack thereof), but also the gradient uniformity (or lack thereof), and the specific aperture(s) of the transmit and receive coils. The apertures of the transmit and receive coils serve to define the lateral extent of the individual iso-$B_0$ slices but not the surface contour.

Regardless of the geometrical configuration of the slice (so-called Iso-$B_0$ surfaces), it is the gradient direction—whether by deliberate application or as a result of the non-linear B field—which differentiates the various slices from one another in the Larmor frequency domain.

Samples can be acquired in a variety of ways. A few examples follow:

2D Stimulation

In a homogeneous magnetic field system, a slice selection gradient $G_{ss}$, defined as $$G_{SS} := \frac{\partial B_z}{\partial z}$$

is applied. Selective slices of location $Z_0$ and width $\Delta Z$ are stimulated through an appropriately shaped apodized waveform of the form $$A \frac{\sin(2\pi f_\Delta t)}{2\pi f_\Delta t} \cos(2\pi f_L t)$$

The slice thickness $\Delta Z$ is selected, for a given slice select gradient $G_{ss}$ by choosing $f_\Delta$ to be given by $$f_\Delta := \gamma \cdot G_{ss} \cdot \Delta Z$$

and the specific slice center $Z_0$ is selected by choosing $f_L$ to be given by $$f_L := \gamma \cdot (B_0 + G_{ss} \cdot Z_0)$$

In this case, $f_L$ corresponds to the Larmor frequency at the center of the slice at $Z_0$. $\gamma$ corresponds to the gyromagnetic ratio, which is approximately 4.258 kHz/G for $^1$H. This is made clearer by examining the associated Fourier transform as $$\mathcal{F}\left(A \frac{\sin(2\pi f_\Delta t)}{2\pi f_\Delta t} \cos(2\pi f_L t)\right) = \frac{A}{4f_\Delta} \cdot \left(rect\left(\frac{f - f_L}{f_\Delta}\right) + rect\left(\frac{f + f_L}{f_\Delta}\right)\right)$$

where $$rect(f) := \begin{cases} 1 & |f| \le 1 \\ 0 & \text{otherwise} \end{cases}$$

In 2D Spin Echo (SE) MRI applications, the remaining two axes, which we refer to as 'X' and 'Y', are usually encoded with a frequency gradient assigned to one, and a series of phase gradients assigned to the other, so as to generate enough information to localize a specific voxel in 3D space. Without loss of generality, we will assign the 'X' axis to correspond to the frequency gradient axis, and the 'Y' axis to correspond to the phase encoded axis.

In normal MR Imaging, a phase slope is set for each 'Y' value, a frequency gradient is applied to the 'X' axis, and the resulting echo is sampled and stored along a row in the k-space matrix. In this way, the entire k-space matrix is filled for a given slice. A 2D Fourier transform is then applied to these samples and the resulting magnitude creates the image.

To be mathematically precise, the total received signal after being stimulated by the slice-select RF pulse can be expressed as:

$$S(t) = \iint \rho(x,y) e^{j\phi(x,y,t)} dx dy$$

where $$\phi(x,y,t) := 2\pi\gamma(\int B_0 dt + x\int G_x(t)dt + y\int G_y(t)dt)$$

represents the phase component of the signal over x, y and t (time), and $G_x$ & $G_y$ represent the magnetic field gradient signals $$\frac{\partial B_z}{\partial x} \text{ and } \frac{\partial B_z}{\partial y}$$

respectively.

The explicit time-dependence of $G_x$ & $G_y$ on t is to take into account the fact that the gradient signals are adjusted to select the desired phase lead/lag. The first term in the $\phi(x, y, t)$ expression is merely the integral of the Larmor frequency.

If we make a few substitutions, the equation for $S(t)$ becomes a little more clear.

Let $$k_x(t) := \int G_x(t) dt; \; k_y(t) := \int G_y(t) dt$$

Substituting into the $S(t)$ expression yields $$S(t) = \iint \rho(x,y) e^{j2\pi\gamma(\int B_0 dt + xk_x(t) + yk_y(t))} dx dy \\ \iint \rho(x,y) e^{j2\pi\gamma \int B_0 dt} e^{j2\pi\gamma(xk_x(t) + yk_y(t))} dx dy$$

This can be further rearranged as follows:

$$S(k_x(t), k_y(t)) e^{j2\pi\gamma \int B_0 dt} = e^{j2\pi\gamma \int B_0 dt} \iint \rho(x,y) e^{j2\pi\gamma(xk_x(t) + yk_y(t))} dx dy$$

The left-hand portion of this equation represents the standard "k-space" signal as a function of time, modulated by the corresponding Larmor frequency. The right-hand portion of the equation shows that this is simply related to $\rho(x, y)$ by the 2D Fourier transform across $k_x$ & $k_y$, also as a function of time, and also modulated by the Larmor frequency.

In one implementation, we are ultimately not interested in variations in the 'X' or 'Y' planes, but we are interested in the total signal resulting in each plane located at $Z_0$.
More simply put, we want the resulting signal when $k_x=k_y=0$. This will result in $$S(0,0)e^{j2\pi \gamma fB_0 dt} = e^{j2\pi \gamma fB_0 dt} \iint \rho(x,y)dxdy$$

But this is simply the signal measured at $k_x, k_y=0, 0$ in k-space. To obtain this from a standard MR imaging machine, we need to have access to the "raw" k-space data, and simply extract the value at (0, 0).

Now, it is entirely possible that the resulting value is complex-valued. As such, it would be prudent to examine the magnitude of the resulting signal as $$\sqrt{S(0,0) \cdot S^*(0,0)}$$

where the superscript asterisk denotes complex conjugation.

As a side-note, while this discussion has been focused on the variation of these values as a function of z, it is also possible to take the same approach by examining the values across the x-axis (i.e. along the frequency gradient) and then combine the same locations across the range of z-values.

While the prior discussion refers to the conventional MRI 2D slice acquisition technique—3D MRI acquisition techniques can also be used to acquire the slice by slice signals from the sample.

Regardless of how the data is obtained, a value for each slice will have an associated strength to it, which is proportional to the content of the NMR producing substance (e.g., marrow) in that slice. The smaller the signal, the less marrow (and presumably the more substance with a lower signal [e.g., bone]) occupying that slice.

Energy is another way to describe and analyze the signals that come from the NMR producing materials in the sample. Energy is a scalar value as opposed to the signal which can be complex (i.e., have differing phase relations).

Figure 3:
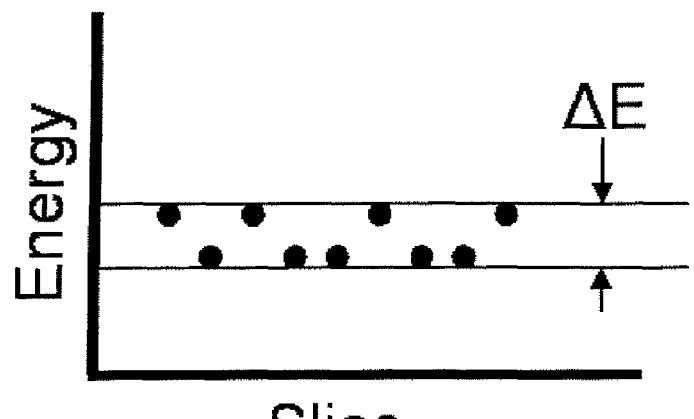
FIG. 3 is a hypothetical plot of the Energy observed at slice n for all of the slices for which data is acquired.

If one plots E(n), the Energy observed at slice n, for all of the slices acquired, one might get the plot of FIG. 3.

Figure 4:
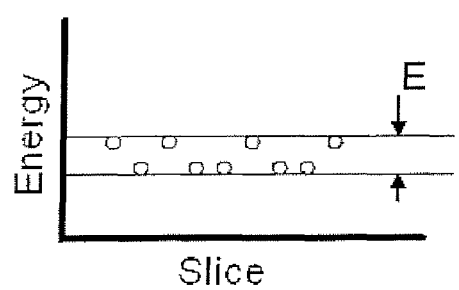
FIG. 4 presents plots similar to that of FIG. 3, but with large variations between slices, suggesting there is a varying amount of marrow within each slice.
Figure 4:
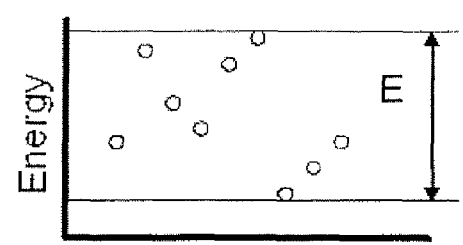

Note that the following discussion refers to marrow in bone as an example—the analysis also applies to other multi phase mixtures with significantly different NMR signals. What is of interest is the variation in this signal level as the various slices are examined. If the energy for each slice is largely the same as the next, this suggests that the energy level within each slice is largely the same (i.e. the same total amount of marrow exists within each slice). On the other hand, if there are large variations between slices as in FIG. 4, this suggests there is a varying amount of marrow within each slice.

Figure 5:
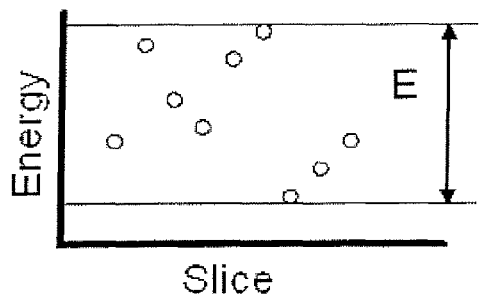
FIG. 5 presents plots illustrating how rapidly the energy changes, slice to slice, a slowly changing energy level suggesting an underlying structure which is different than a more rapidly varying one.
Figure 5:
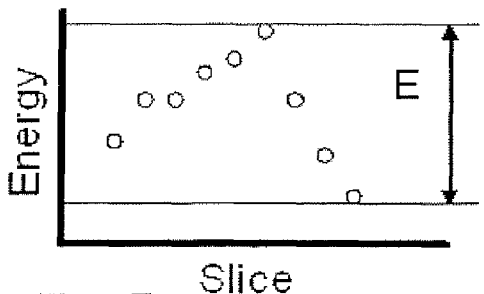

But another important aspect is how rapidly the energy changes between slice to slice. A slowly changing energy level suggests an underlying structure which is different than a more rapidly varying one (see FIG. 5).

One can determine the slice thickness as well as the inter-slice spacing (through the use of the gradient slope, the receive bandwidth, and the transmit frequency), therefore one can relate the 'speed' with which the energy level changes, to the inter-slice dimension.

Figure 6:
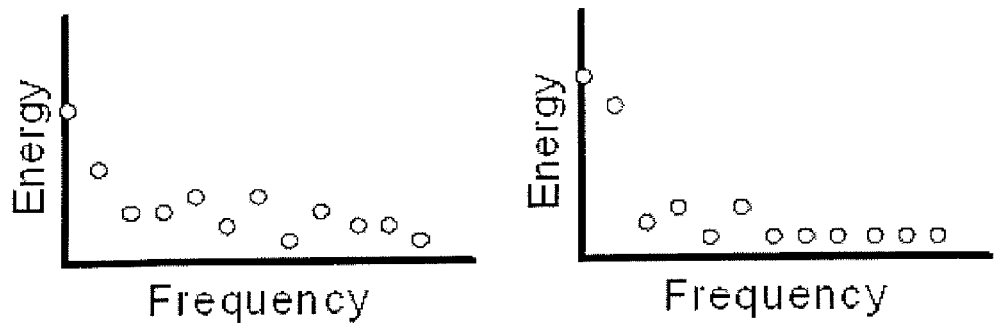
FIG. 6 presents plots of the magnitude of the Discrete Fourier Transform for the energy plots of FIG. 5.

This suggests examining the resulting energy-vs-slice graph in the frequency domain (i.e. take the Fourier transform of E(n). Note that this frequency domain is different from the Larmor frequency domain used to differentiate the slices, but as shall subsequently be seen, they're related in an interesting and useful way). For the previous E(n) graphs, the corresponding Fourier transform graph (actually, this would be the magnitude of the Discrete Fourier Transform) might look like FIG. 6.

By inspection, we can see that the graph on the right has more of the energy concentrated in its lower frequencies, whereas the graph on the left has its energy more distributed into the higher frequencies. Given that a lower frequency variation is a possible indication of larger "pockets" of marrow (and therefore more widely spaced trabecular structure—or larger or more elongated pockets of crude oil in rock), we would be interested in identifying this in comparative samples.

Taking a step back for a moment then, what is being done is to first examine the values $S_n(0, 0)$ for each slice n, of an underlying continuous function $S_z(0, 0)$, then examining the corresponding periodic structure by taking the Fourier transform as follows:

$$V(j\omega) := \int S_z(0,0) e^{-j\omega z} dz$$

Now we need to keep in mind that the signal point $S_z(0, 0)$ values corresponds to the signal corresponding to location z. If instead of extracting these values one at a time corresponding to individual slices, a gradient is applied in the z direction, and the entire volume is stimulated, the resulting time-dependent signal would be:

$$W(t) := \int S_z(0,0) e^{j2\pi \gamma f(B_0 + zG_{ss})dt} dz = \int S_z(0,0) e^{j2\pi \gamma f(B_0 + zG_{ss})t} dz$$

which can be rearranged as $$W(t) := e^{j2\pi \gamma fB_0 t} \int S_z(0,0) e^{j2\pi \gamma z G_{ss} t} dz$$

Let $$\tau := -\gamma G_{ss} t$$

Then $$W\left(-\frac{\tau}{\gamma G_{ss}}\right) := e^{-j2\pi \frac{B_0}{G_{ss}} \tau} \int S_z(0, 0) e^{-j2\pi \tau z} dz$$

Now let $$\Omega := 2\pi \tau$$

Then $$W\left(-\frac{\Omega}{2\pi \gamma G_{ss}}\right) := e^{-j\frac{B_0}{G_{ss}} \Omega} \int S_z(0, 0) e^{-j\Omega z} dz$$

Now the integral is recognized as $V(j\omega)|_{\omega=\Omega}$ as follows:

$$V(j\Omega) = e^{j\frac{B_0}{G_{ss}} \Omega} W\left(-\frac{\Omega}{2\pi \gamma G_{ss}}\right)$$

So, it has been shown that the corresponding Fourier transform of the spectrum of the samples of slices along z (i.e., the spatial frequency spectra) can be obtained directly from the time-generated signal by stimulation in the presence of a gradient, multiplied by a complex exponential whose frequency is related to the magnitude of the $B_0$ field strength, and the z-gradient "slice-select" field strength. This can be done independently of the use of a Fourier transform on the acquired data—the sampled echo is already the spatial frequency (Fourier transform of the slice by slice signal vs Z) that one is looking for.

Now that it has been shown that the Fourier transform spectrum of the distribution of signal (e.g., amount of NMR signal generating material) along the z direction is acquired directly from the NMR experiment described above, now consider details of how to take the data and approaches to quantifying these spectra.

Analysis Technique

Figure 7:
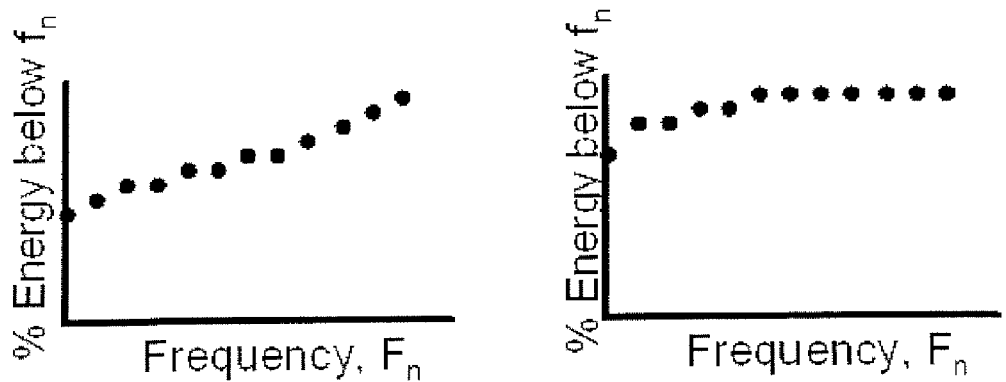
FIG. 7 presents plots of the percentage of energy contained in frequencies≦frequency $f_n$.

Consider now generating a graph which plots the percentage of energy contained in frequencies≦frequency $f_n$. If this was done for the preceding graphs, one might obtain the graphs of FIG. 7.

In this case, the graph on the left clearly shows the effect of non-zero energies in the higher frequency components as compared to the right. If a threshold of e.g. 80% was set and the corresponding frequency was examined, this would give an indication of the frequency wherein 80% of the total energy is contained at or below it. The conjecture is that, as this number gets lower (i.e. most of the energy is concentrated in the lower frequencies), the potentially more diseased the bone is.

The Effect of Sample Size on Data Acquired

Figure 8:
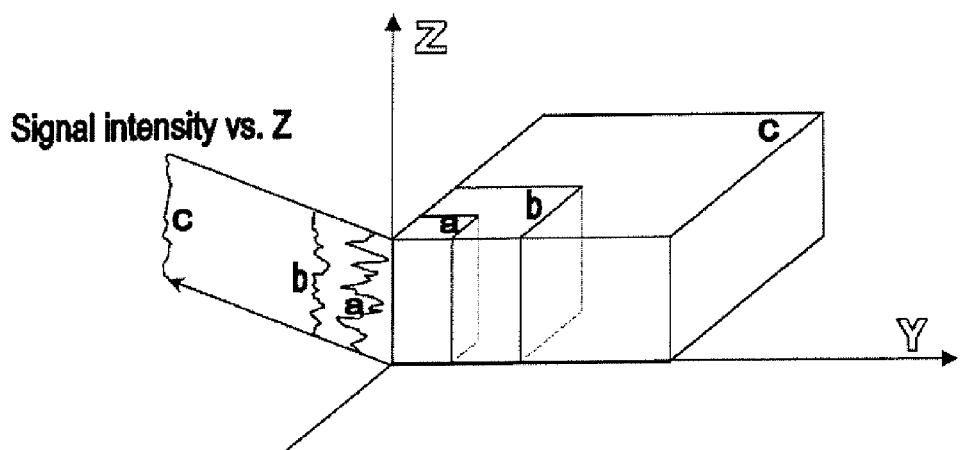
FIG. 8 illustrates the effect sample size relative to the predominate (or characteristic) sizes of the signal producing phase will have on the average value and variability of an echo as a function of z in a one dimensional analysis.

Sample size relative to the predominate (or characteristic) sizes of the signal producing phase will have an effect on the average value and variability of signal as a function of z in a one dimensional analysis. This is illustrated in FIG. 8, where in case a, the sample volume approaches the characteristic size and there is significant variation in the signal value (proportional to the amount of signal producing phase as a function of Z) vs. Z. Case c in contrast has on average a much higher signal level, but a smaller variation in signal level as a function of Z.

By selecting a sample volume which is large enough to sample the characteristic sizes but not so large that large numbers of characteristic sizes are averaged, an optimal sensitivity (hence sample volume) to the desired structure size can be obtained. This is particularly relevant for a system using a single gradient as in the case of a low cost device to assess bone structure in patients or to assess pore size and distribution in oil strata with a NMR device inserted in a bore hole. These two devices, described in more detail later, have in common the use of a fixed gradient generated by the main magnet that is also used for the encoding in the Z direction.

In both these cases, additional information on the anisotropy of the sample can be obtained by moving the gradient direction in the sample. This can be accomplished by physically moving the sample or magnet relative to each other or electrically by modulating the magnetic field. Information on the homogeneity of the sample can be acquired by moving (translating) the sensitive volume around in the sample.

Sample Volume Delineation

Figure 9:
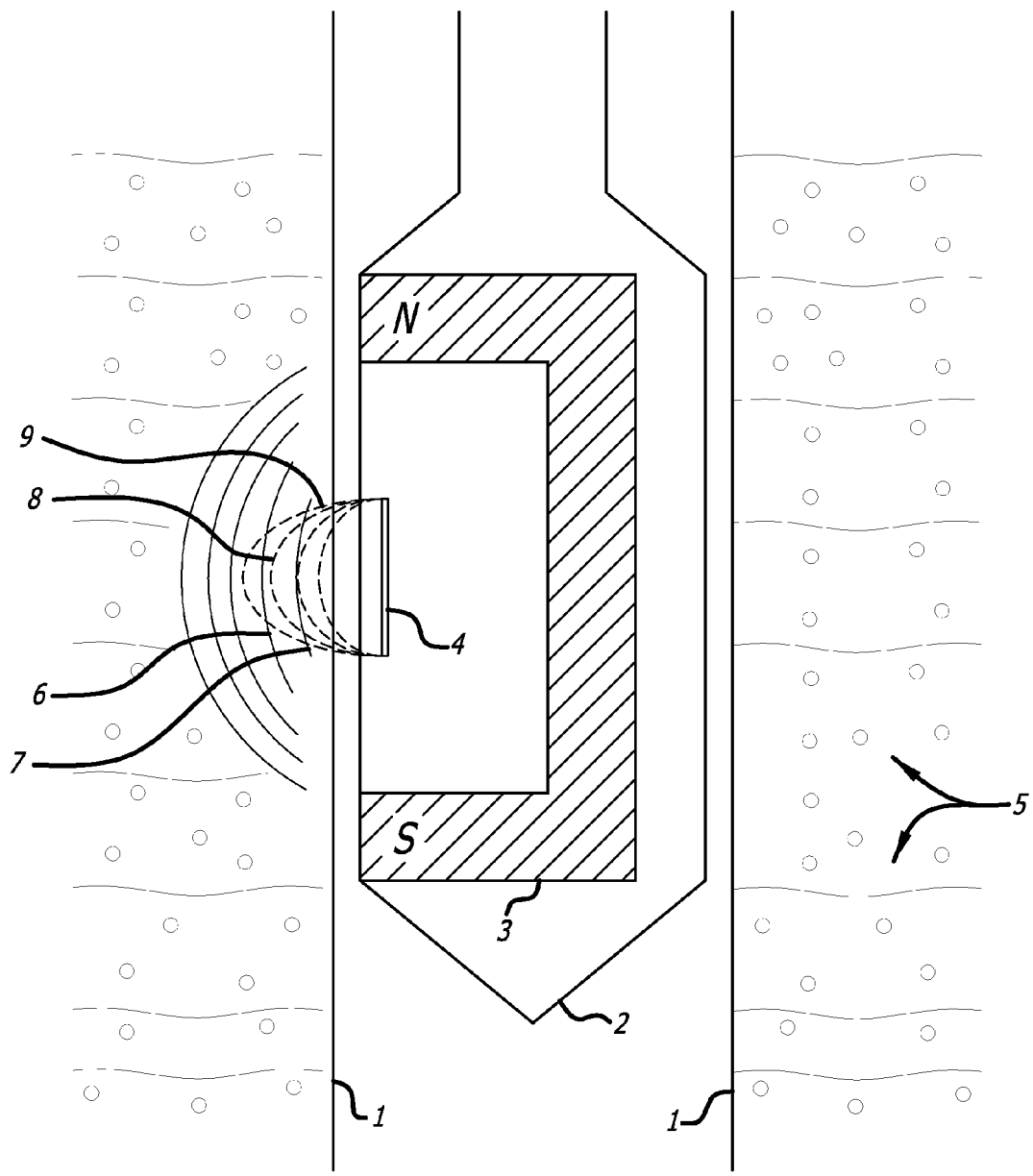
FIG. 9 is a schematic illustration of an implementation of the sample volume delineation showing a bore hole through strata bearing pockets of oil.

In the case of a single gradient system as described above, sample volume delineation is accomplished by a combination of
 receiver bandwidth
 receive antenna (coil) sensitivity function
 transmit B field
 magnet field distribution FIG. 9 is a schematic illustration of an implementation of the sample volume delineation showing a bore hole 1 through strata bearing pockets of oil 5. The device is housed in housing 2 with magnet 3 to generate a series of iso-$B_0$ surfaces 6 and 7 in the strata. A transmit/receive antenna 4 (here shown as a single antenna—could also be implemented with separate transmit and receive antennas) with a sensitivity function indicated by dashed lines 8. The sample volume 9 is delineated by the receiver bandwidth (alternatively or additionally the transmit bandwidth) between iso-$B_0$ surfaces 6 and 7 and by the combined transmit receive minimum sensitivity boundary 8.

This arrangement could be used to assess anisotropy in the plane orthogonal to the bore hole by rotating the probe about the bore hole axis and in planes parallel to the bore hole by modifying the iso-$B_0$ surfaces to be inclined to the bore rather than nominally parallel as shown in FIG. 9. The modification can be accomplished by rotating the magnet 3 or modulating the field with additional electromagnets.

Figure 10:
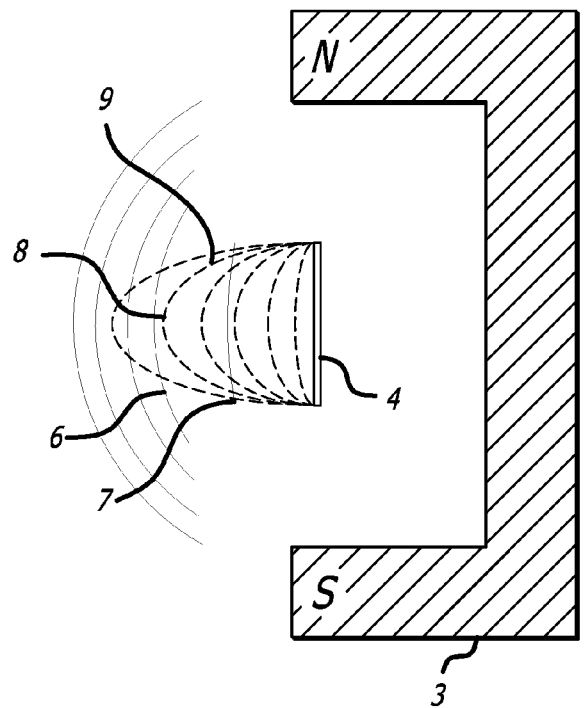
FIG. 10 illustrates a concept similar to that of FIG. 9, but now for assessing trabecular structure in cancellous bone.

FIG. 10 illustrates a concept similar to that of FIG. 9, but now for assessing trabecular structure in cancellous bone. The sensitive volume (sample volume) 9 is then placed in the region of interest in the relevant bone for assessing trabecular structure. Candidate sample locations include the proximal and distal tibia, the distal radius, the calcaneous, the hip, the iliac crest, and the vertebrae.

Figure 11:
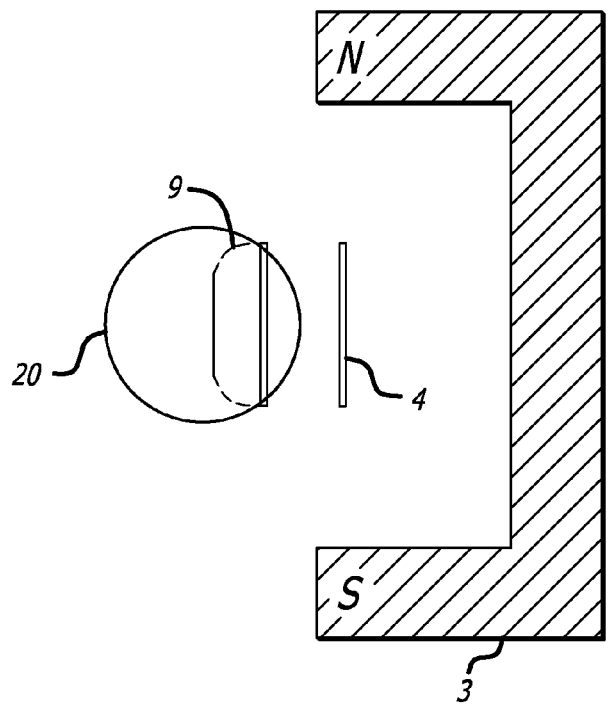
FIG. 11 illustrates positioning the sample volume inside the cortical bone of a candidate anatomical location.

FIG. 11 illustrates positioning the sample volume 9 inside the cortical bone 20 of a candidate anatomical location.

Design features of a device to implement this technique for trabecular bone assessment in human patients would include:

1. a magnet designed to have a nominally constant gradient over the imaged area to provide sensitivity as a function of spatial frequency 2. the ability to sample multiple orientations in the target bone—by mechanically moving the magnet relative to the bone or electrically modulating the field pattern to reorient the iso-$B_0$ surfaces 3. a device to position the anatomy in a repeatable and comfortable way.

4. mechanical or electronic sweeping through 3D space to assess anisotropy and/or locate sentinel directions 5. a controller to generate and drive the transmit antenna 6. receiver system to receive the signal from the sample volume and analyze it This system would evaluate properties including:

7. short range order 8. anisotropy 9. homogeneity 10. characteristic spacing/presence of low spatial frequency structures The second provisional application relates to position resolved spatial frequency spectroscopy, and describes a method for acquiring spatial frequency spectra (SFS) measurements at localized regions in a 3 dimensional sample. This approach is an extension of spectroscopic MRI techniques. ("NMR chemical shift imaging in three dimensions", T. R. Brown et al., Proc. Natl. Acad. Sci. USA, 79:3523 , 1982) Hornak provides a description of these various methods in "The Basics of MRI" (Joseph P. Hornak, Ph.D., Copyright 1996-2006), which is incorporated herein by reference. Also described by P. A. Bottomley "Spatial localization in NMR spectroscopy in vivo." *Ann. NY Acad. Sci.*508:333 (1987). Both of the foregoing references are hereby incorporated by reference.

Figure 17:
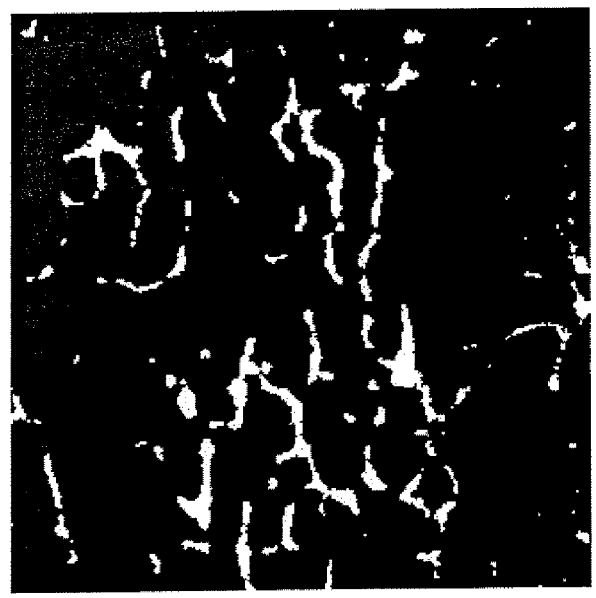
FIG. 17 showing 2D CT image above and 2D Fourier transform with two directions indicated showing the anisotropy in the image and the 2DFT.
Figure 17:
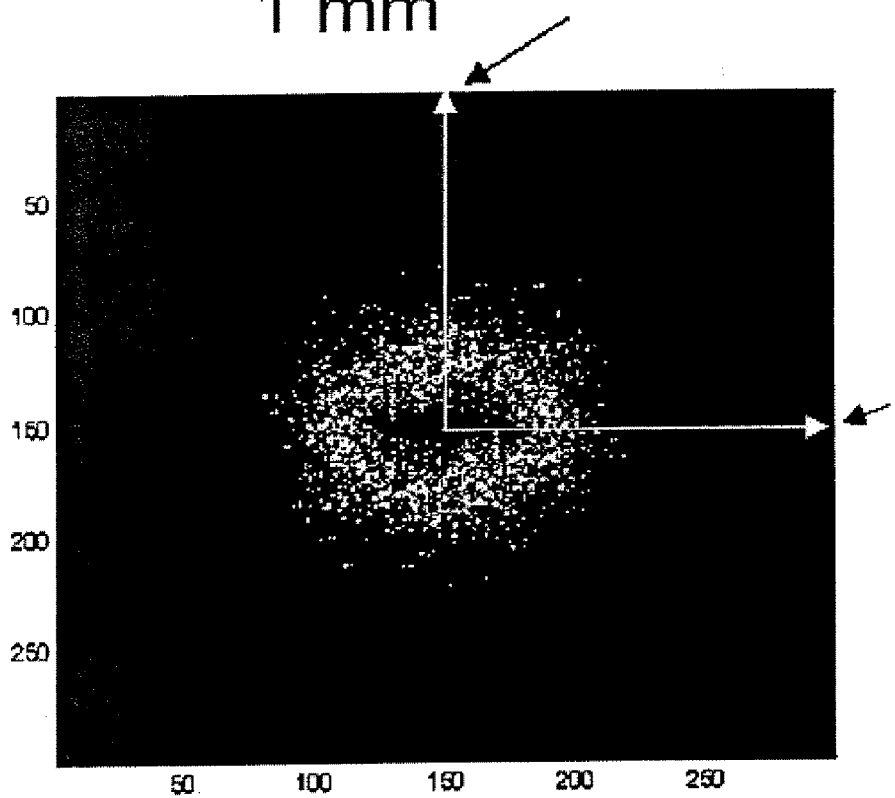
Figure 18:
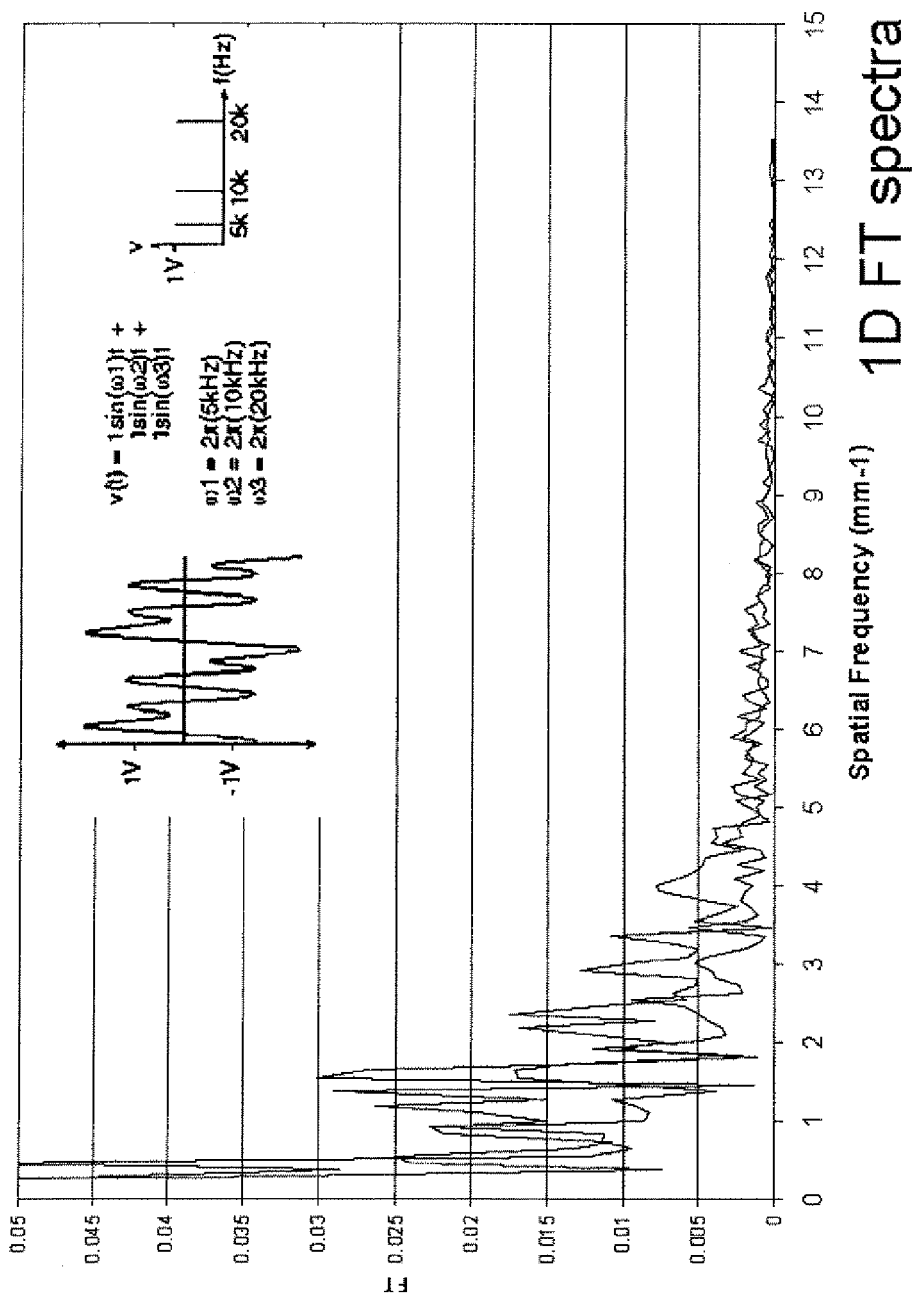
FIG. 18 shows two spatial frequency spectra corresponding to the two arrows indicated in the 2D FT of FIG. 17, illustrating the significant differences at spatial frequencies less than 5 inverse mm.

Spatial frequency spectra (SFS) contain (represent) the power spectrum of the distribution of dimensions in the sample. This disclosure further describes the use of spatial frequency spectroscopy for the assessment and diagnosis of normal and abnormal medical conditions. The application to osteoporosis is described in the pending utility application Ser. No. 11/064,381 filed Feb. 23, 2005 and is incorporated herein by reference. The use of spatial frequency spectroscopy for assessment of disease (health) is independent of the source of the SFS. SFS can be extracted from Magnetic resonance as well as by Fourier transform analysis of 3D and 2D images of anatomical structures desired to be analyzed. FIG. 17 and 18 illustrate the generation and analysis of SFS from a 2D computed tomography high resolution image of trabecular bone from a vertebra. The anisotropy clearly visible in the image is clearly revealed in the 2D FT and individual spectra in FIG. 18.

Figure 19:
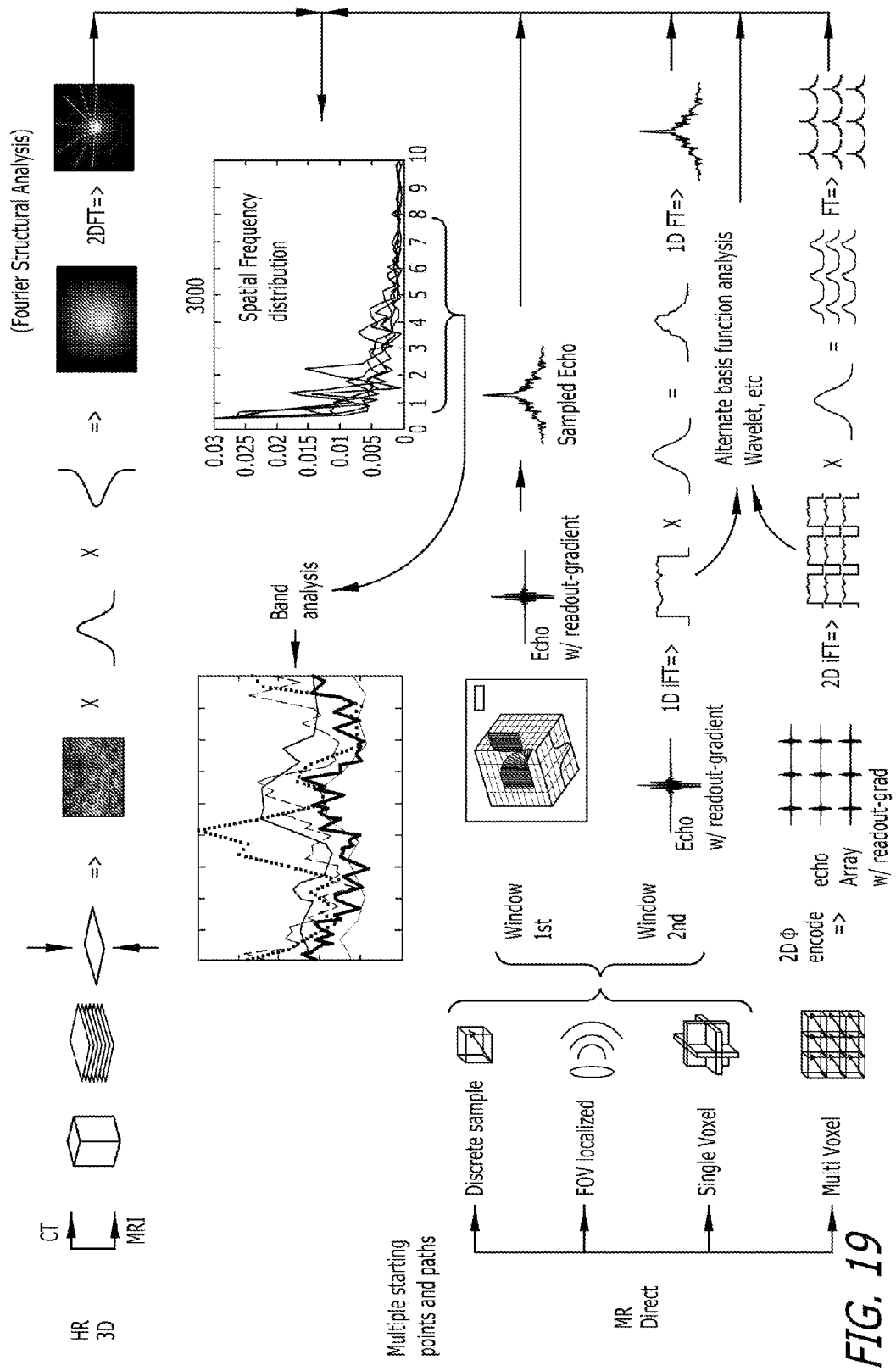
FIG. 19 is an illustration of various exemplary techniques for obtaining and analyzing data in accordance with the present invention.

A somewhat similar technique is illustrated in the top line of FIG. 19 (labeled HR 3D, or high resolution 3D). There two dimensional data for a series of slices of a sample are taken, e.g., data acquired by a computed tomography (CT) device. The stack of images constitutes a 3D model of the structure. Rather than analyze the 3D data using conventional morphology evaluation methods in this alternate approach a region of the three dimensional data is collapsed (projected) into two dimensional data by summing the data in one dimension and then windowed in both dimensions, which when plotted in two dimensions, provides a plot (image) as shown. Now a two dimensional Fourier transform is taken to provide a two dimensional plot of echo intensity versus position in the projected image, shown in FIG. 19 as radial values from a central value. It has been shown using preexisting data from in-vitro samples that analysis of the structure by Fourier or other (e.g., wavelet analysis) is a valid way to analyze and characterize the structure, as it provides good correlations with bone strength.

Current spectroscopy methods (which are designed to generate an NMR spectrum from a localized region or regions in the sample) do not utilize an applied readout gradient. This is by design so that a true NMR spectrum can be obtained from the region of interest. Imaging protocols (by contrast to spectroscopy methods) typically use an applied gradient during readout of the echo so as to generate a full line in k-space for each echo, hence facilitating rapid image acquisition.

For the case in imaging protocols where the line in k-space passes through the origin, the acquired data is a spatial frequency spectra (SFS) from the sample in the direction of the gradient. (For imaging protocols, the gradient is generally orthogonal to the other encode axes so that rectangular image pixels or voxels can be reconstructed.)

The method disclosed here is directed at gathering a spatial frequency spectrum (or spectra) in one or more vector directions in the 3D sample. To accomplish this—the disclosed method utilizes a readout gradient with the direction of the gradient aligned with the direction desired to be analyzed for spatial frequencies in conjunction with localization methods as currently utilized in NMR spectroscopy (as described in Hornak and above). The use of a read-out gradient to generate a spatial frequency spectrum is described in the provisional application reproduced above.

Figure 12:
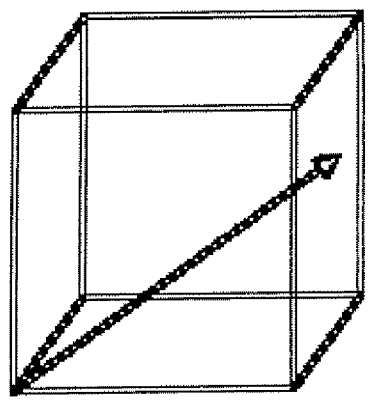
FIG. 12 cubic sample showing application of read-out gradient in desired direction.

The difference between the techniques disclosed here and 3D imaging is two fold. First, the readout gradient is not necessarily applied in a direction orthogonal to the phase encoded directions, but rather in the vector direction for which the spatial frequency spectra is desired. This is illustrated for a simple case of an isolated sample in FIG. 12 and illustrates the case of a sample for which the spatial frequency spectra (SFS) is desired in the direction indicated by the arrow.

Figure 13:
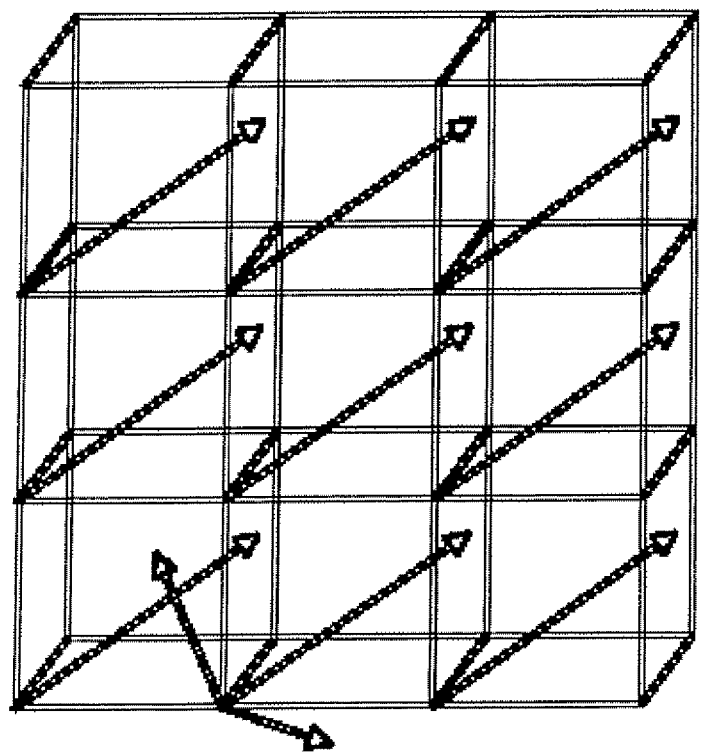
FIG. 13 slab sample showing application of readout gradient in desired direction and that sample has been divided into 6×6 array using one of the methods described.
Figure 14:
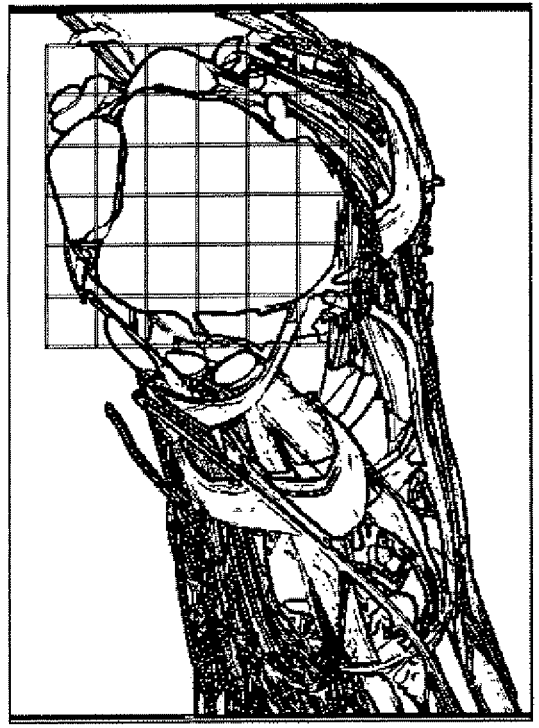
FIG. 14 illustrating slab selection in the distal tibia and a 6×6 array delineated by phase encoding.
Figure 14:
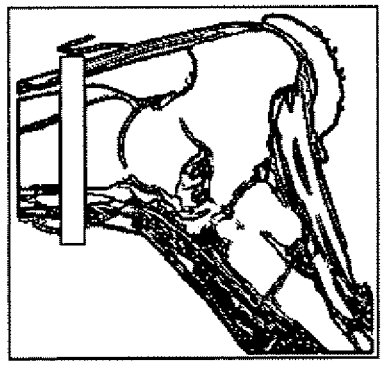

FIG. 13 illustrates the case where a map of the SFS is desired for a number of voxels. FIG. 14 illustrates application of this mapping method to a slab taken through the distal tibia.

Prior art for position resolved NMR spectroscopy (for which there are several methods) has developed methods for localizing the region from-which to receive an NMR echo in a homogenous field. In its simplest abstraction, this innovation can use any of the prior art spectroscopy methods with the addition of a gradient during readout of the echo. Directly sampling this echo will provide the SFS data desired.

Figure 16:
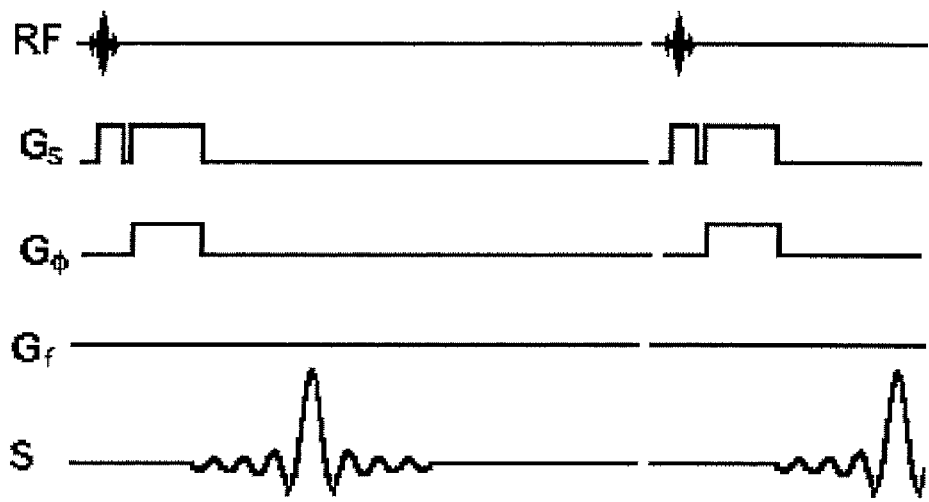
FIG. 16 pulse sequence used in a spatial-spatial-spectral spectroscopy method.

An exemplary Spectroscopic Imaging (NMR) Technique is based on the 3-D or volume imaging technique, with a few modifications. With reference to FIG. 16, the RF pulse is volume selective and the readout gradient ($G_f$) is turned off. The gradients labeled $G_s$ and $G_{phi}$ are cycled through their range of values to record spectra from all points in the spatial-spatial domain.

The SFS technique disclosed here follows the Spectroscopic imaging technique described above but with the addition of an applied readout gradient during the echo. The purpose of the readout gradient is to gather spatial frequency spectra at each of the locations in the imaged volume. The use of a readout gradient to acquire a spatial frequency spectra is described in the first provisional patent application above.

Figure 15:
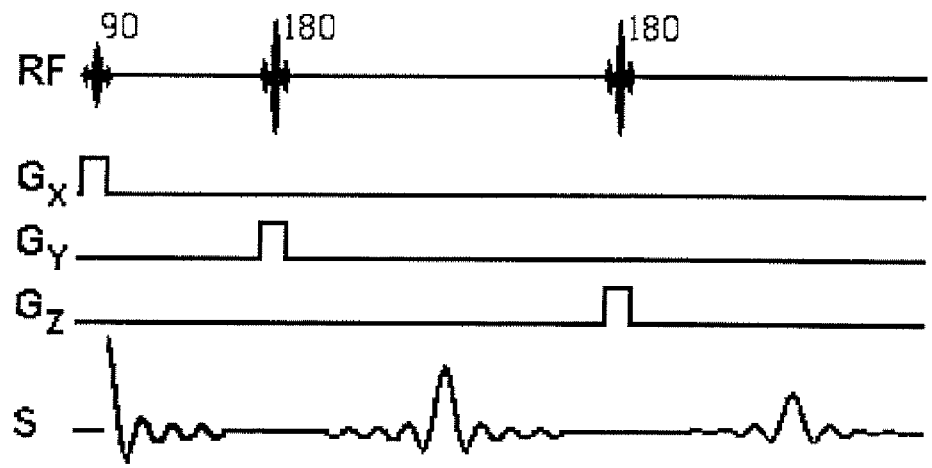
FIG. 15 pulse sequence used in PRESS spectroscopy method.
Figure 15:
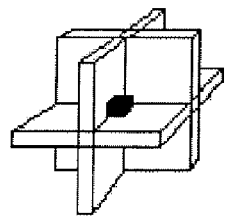

Another likely implementation of the disclosed position resolved SFS is to use a modification of the "Point resolved spectroscopy" (PRESS) method. The PRESS pulse sequence is illustrated in FIG. 15. This sequence with the addition of a read-out gradient applied in the direction of the desired SFS will produce an echo with the SFS information as described in the first provisional Application above. Alternatively to using a readout gradient (frequency encode), one could apply a phase encode to a selectively excited voxel to acquire a single spatial frequency measurement.

Now referring to FIG. 19 again, specific examples of the application of the present invention to sample structure analysis may be seen. Using direct magnetic resonance (MR direct) as opposed to high resolution 3D imaging magnetic resonance (HR 3D), the first task is to define the sample to be analyzed. This may either be a discrete sample defined in 3D sample space (physically separated from the structure from which it came), a field of view (FOV) localized sample, or a single voxel. In the case of a field of view localized sample, the samples are in the form of planes of uniform magnetic field intensity, with a gradient in the field intensity in a direction perpendicular to the planes. The planes may be flat (see FIG. 1, for example) or curved (see FIG. 2, for example). In such a case, the typical RF excitation will excite the resonant spin frequency, which frequency will vary plane to plane because of the magnetic field difference, plane to plane. Consequently the echo again will represent the frequency components of the signal intensity with distance within the field of view and through a depth range defined by the range of the RF excitation and the magnetic field strength and gradient. Obviously in this technique, the field of view may be defined at least in part by the size, etc. of the RF excitation coil and the echo pickup coil, if separately provided.

A single voxel within the sample space may be isolated by techniques well known in the prior art, generally using combinations of frequency gradients due to field gradients in the sample, which techniques are hereinbefore described and well known in the art. In that regard, a single voxel should be chosen large enough to include the desired variations in the structure for adequate analysis for multiple voxels. As subsequently described in greater detail, a single voxel method may be used with only two slice select sequences when the third orthogonal direction is the one to be sampled. In this case, the receiver bandwidth will define the volume in the third direction. The Window $2^{nd}$ method described below may use a sample selection technique to in effect sample a line of voxels.

If desired, multiple voxels may be used to provide a two dimensional echo array. Inverse Fourier transforms can be applied to the resulting echo, the results windowed and the windowed results Fourier transformed for-analysis. Also here as well as in the other techniques described herein, other transforms may be used if desired, such as, by way of example, wavelet transforms as previously mentioned.

An important aspect of the present invention is to somehow provide windowing in the results to minimize certain adverse affects. Windowing has been used in other disciplines to minimize the intrusion of frequency components from effects other than the desired signal itself. By way of but one example, it is well known that any repetitive waveform may be represented by a Fourier series by taking one full period of the waveform and Fourier transforming the same. However, if the period of the waveform is not accurately known, then the Fourier transform may be inadvertently performed on a segment of that waveform which is less than one full period, or alternatively, greater than one full period. Therefore the beginning and the end of that segment, taken over the wrong period for the repetitive waveform, will typically have different values, appearing to be a step change within the waveform. The resulting Fourier transform will be the Fourier transform of a repetitive wave of the wrong period and having a repetitive step change therein, thereby injecting frequency components into the Fourier transform not present in the true waveform. By windowing the segment by shaping the amplitude of the segment, usually by having the ends of the waveform segment smoothly decrease to zero or near zero, this effect is minimized, with a more accurate Fourier transform resulting. Numerous windowing functions are well known, with the choice of the windowing function to be used typically being a combination of analysis of the application and personal preferences regarding windowing functions. Typically, but not necessarily, a fixed shape window function such as, by way of example, a Hanning, Hamming or Blackman window function would be used.

Referring back to FIG. 19 (MR Direct), it will be noted that two paths for proceeding with the windowing function are shown, these two paths being labeled Window $1^{st}$ and Window $2^{nd}$. In the case of Window $1^{st}$, considering either a discrete sample or the field of view localized sample, a magnetic field gradient is established through the sample and excitation is provided by an RF signal of an appropriate frequency band, which is then terminated and the echo recorded. Normally the RF signal would be of equal amplitude throughout the desired frequency range so as to excite all parts of the sample. In Window $1^{st}$, the amplitude and phase of the RF excitation versus frequency is itself tailored so that the echo itself is windowed across the sample. This is not quite the same as windowing the RF frequency itself, but rather is done be controlling the amplitude and phase of the RF signal to provide an echo which itself has the desired predetermined windowed properties, i.e., calculating backwards to determine the required RF amplitude and phase with frequency to obtain the windowed result. While this provides the desired windowing and provides signal intensity versus distance for direct analysis, the technique itself is not preferred. One reason is that while it windows the echo signal as desired, it does not window the noise in the echo. Consequently, the signal to noise ratio is unnecessarily low at or near the extremes of the echo frequencies.

In the case of Window $2^{nd}$, an RF excitation is applied to the sample to excite the Larmor frequency(s) and then, while a field gradient is applied to the sample, the echo is measured. Note that the sample could be subjected to a band of RF frequencies while a field gradient is imposed, or a single RF frequency applied while the magnetic field is uniform to excite the same Larmor frequency in all parts of the sample, and then a field gradient imposed to separate the Larmor frequencies before the echo is measured. This technique takes advantage of the fact that changing a parameter determining the resonant frequency of a system previously excited does not stop the decay-of the resonance, but simply changes the frequency at which the resonance will decay.

The echo signal obtained constitutes a band of frequencies, each frequency corresponding to the Larmor frequency at a "position" in the sample. For an entire slice, the position is measured perpendicular to the surfaces of the slices. For a more definitive sample, which may be defined using any of well-known techniques, the position may be perpendicular to the surfaces of the slice, with each slice having one dimension intentionally limited in comparison to the third dimension, or with a two dimensional limitation on each "slice", essentially defining a sample stick or wedge, essentially a line of voxels, or a rectangular sample. When phase encoding is used, both the amplitude and phase of each frequency in the echo must be considered.

The amplitude (and phase) of each frequency in the echo may be plotted against the frequency itself over a respective range of frequencies. However, any frequency (and phase) represents a position in the sample. Consequently the plot of echo signal amplitude (and phase) of each frequency versus frequency may be considered a plot of echo signal amplitude (and phase) of each frequency versus position in the sample. But this is simply the Fourier transform of a repetitive wave of echo signal versus position, the wave repeating each increment in position equal to the corresponding frequency range in the echo signal analyzed.

In the Window $2^{nd}$ technique, the inverse Fourier transform of the echo signal is taken, which provides echo signal intensity versus position in the sample. The echo itself is the Fourier transform of the signal intensity with distance, with the inverse Fourier transform yielding the signal intensity versus distance. Note that the signal intensity versus distance has sharp edges because of the cutoff frequencies either in the excitation, in the echo receiver, or both. The variation in the top of the wave resulting from the one-dimensional inverse Fourier transform is a combination of the signal and background noise. Now when a windowing function is applied for the purpose of analyzing the spatial frequency content of the wave, the shape of the signal (and noise) versus distance is a waveform having a general shape of the windowing function, though with the desired signal (and noise) thereon. Note that in Window $2^{nd}$, the windowing function is effectively applied to the combination of the signal intensity and noise, thereby not affecting the signal to noise ratio. Accordingly, the windowing function is applied equally to the two so that the signal to noise ratio is maintained throughout the range of the windowing function. Once the windowing function has been applied, the results may be analyzed by first performing a one dimensional Fourier transform (1D-ft) thereon, or using some other basis function analysis, such as, by was of example, a wavelet analysis. A spatial frequency and/or a band analysis or similar analysis will provide information that may be compared to the corresponding information for healthy bone and bone a various stages of disease to determine the state of the bone examined. The results may also be used to compare with previous results for the same bone to determine the extent or progression of disease.

A method of obtaining desired sample data is to use an abbreviated volume selection procedure for the selective volume excitation routine. This is in comparison to using three selective excitation pulses (90, 180, 180) and then a readout gradient to generate an echo, as is done (without the readout gradient) in the volume selective spectroscopy routine as described in Hornak. An attractive alternate is to use two selective excitations (90 and one 180) to selectively excite a rectangular "stick" in the sample then apply the readout gradient in the third orthogonal direction. The echo generated by this will be the Fourier transform of the signal intensity as a function of position along the stick. It is then a simple exercise to inverse transform the data into "linear space" and locate the region of interest in the profile. This is, in essence a Window $2^{nd}$ in accordance with FIG. 19.

The advantage of doing just the two selective excitation sequences is that it can be done more quickly and there is less signal loss due to T2 de-phasing. The disadvantage is that since it is a prism, if one applies a readout gradient in a direction other than the third orthogonal direction, the sampled volume will be other than a well defined rectangular volume. Hence getting one dimensional profiles in multiple directions will require doing a complete experiment for each direction. This may not be much of an issue, as multiple samples for each direction may be appropriate to get good signal to noise ratios.

The foregoing techniques preserve the essence of the preferred embodiments of the present invention, namely to provide methods for obtaining and analyzing data to determine characteristics of structures, which methods are relatively simple and quick, and do not require the obtaining of data suitable for, or the reduction of such data to provide, actual visually perceivable images of the structure. In essence, the techniques of the present invention provide a "signature" of the sample structure being analyzed that, by comparison with the same signature for similar structures of a range of known conditions (health, oil content, etc.), the sample structure being analyzed may be characterized by that comparison, all without a visual image of the structure, and even without data from which a visual image could be generated, if desired. In preferred embodiments, a one-dimensional echo sample is taken and analyzed, resulting in very fast data acquisition with minimum restrictions on the patient. If multiple samples are taken, the patient may be kept motionless, though if each echo sample is analyzed separately and then the results averaged, moderate patient motion will not matter. Similarly, echoes taken at different angles also may be treated independently, again not requiring complete immobility of the patient.

While certain preferred embodiments of the present invention have been disclosed and described herein for purposes of illustration and not for purposes of limitation, it will be understood by those skilled in the art that various changes in form and detail may be made therein without departing from the spirit and scope of the invention.

What is claimed is:

1. A method of assessing a spatial frequency distribution within a sample of a structure comprising:
    a) subjecting the sample to a magnetic field;
    b) subjecting the sample to magnetic resonance excitation;
    c) receiving an echo signal from the sample while the sample is subjected to a magnetic field gradient;
    d) taking an inverse transform of the received echo signal to obtain an echo signal intensity in one dimension;
    e) identifying a region of interest in the echo signal intensity in one dimension;
    f) windowing the region identified in e) to shape the echo signal intensity in the region of interest;
    g) taking a transform of the windowed echo signal intensity in one dimension obtained in f); and,
    h) analyzing the one dimensional spatial frequency content in the transform obtained in g) in order to access a one dimensional spatial frequency distribution within the sample of the structure without having to acquire all of the data required to create an image.

2. The method of claim 1 wherein the structure is a bone structure.

3. The method of claim 1 wherein the structure is petroleum dispersed in strata.

4. The method of claim 1 wherein the structure is a biologic structure.

5. The method of claim 1 wherein the transform obtained in g) is a Fourier transform.

6. The method of claim 1 wherein the transform obtained in g) is a wavelet transform.

7. The method of claim 1 wherein analyzing the spatial frequency content in the transform obtained in g) comprises comparing spatial frequency distribution in the transform obtained in g) with spatial frequency distributions of transforms of a same type of structure, but of differing characteristics.

8. The method of claim 1 wherein analyzing the spatial frequency content in the transform obtained in g) comprises comparing content of frequency bands in the transform obtained in g) with frequency bands of transforms of a same type of structure, but of differing characteristics.

9. The method of claim 1 wherein:
    in b), subjecting the sample to magnetic resonance excitation comprises subjecting the sample to first and second excitations to excite a stick shaped region in the sample;
    in c), receiving an echo signal from the sample while the sample is subjected to a magnetic field gradient comprises receiving an echo signal from the stick shaped region while the sample is subjected to a magnetic field gradient; and,
    in f), windowing the region identified in e) to shape the echo signal intensity in the region of interest comprises windowing the region identified in e) along the stick shaped region to shape the echo signal intensity in the region of interest along the stick shaped region.

10. The method of claim 1 wherein in d), taking an inverse transform of the echo signal comprises taking an inverse Fourier transform of the echo signal.

11. A method of assessing at least one spatial frequency characteristic of a sample of a structure comprising:
    a) subjecting the sample to a magnetic field;
    b) subjecting the sample to first and second RF excitations to excite a stick shaped region in the sample;
    c) receiving an echo signal from the stick shaped region while the sample is subjected to a magnetic field gradient;
    d) taking an inverse transform of the received echo signal to obtain an echo signal intensity in one dimension;
    e) identifying a region of interest in the echo signal intensity in one dimension;
    f) windowing the region identified in e) along the stick shaped region to shape the echo signal intensity in the region of interest along the stick shaped region;
    g) taking a transform of the windowed echo signal intensity in one dimension obtained in f); and,
    h) analyzing the one dimensional spatial frequency content in the transform obtained in g) in order to access a one dimensional spatial frequency distribution within the sample of the structure without having to acquire all of the data required to create an image.

12. The method of claim 11 wherein the RF excitation includes a band of frequencies, and the magnetic field gradient is imposed before termination of the RF excitation.

13. The method of claim 11 wherein the transform in g) is a Fourier transform.

14. The method of claim 11 wherein the transform in g) is a wavelet transform.

15. The method of claim 11 wherein the structure is a bone structure.

16. The method of claim 11 wherein the structure is petroleum dispersed in strata.

17. The method of claim 11 wherein the structure is a biologic structure.

18. The method of claim 11 wherein in h), analyzing the one dimensional spatial frequency content in the transform obtained in g) comprises comparing spatial frequency distribution in the transform obtained in g) with spatial frequency distributions of transforms of a same type of structure, but of differing characteristics.

19. The method of claim 11 wherein analyzing the one dimensional spatial frequency content in the transform obtained in g) comprises comparing content of frequency bands in the transform obtained in g) with frequency bands of transforms of a same type of structure, but of differing characteristics.

* * * * *